US008974488B2

(12) United States Patent
Tan et al.

(10) Patent No.: US 8,974,488 B2
(45) Date of Patent: Mar. 10, 2015

(54) DELIVERY ASSEMBLY FOR OCCLUSION DEVICE USING MECHANICAL INTERLOCKING COUPLING MECHANISM (75) Inventors: Jianfong Tan, Singapore (SG); Ping Ye Zhang, San Diego, CA (US)

(73) Assignee: Achieva Medical Limited, Grand Cayman (KY)

( * ) Notice: Subject to any disclaimer, the term of this patent is extended or adjusted under 35 U.S.C. 154(b) by 589 days.

(21) Appl. No.: 13/265,198

(22) PCT Filed: Apr. 19, 2010

(86) PCT No.: PCT/US2010/031606
§ 371 (c)(1),
(2), (4) Date: Oct. 19, 2011

(87) PCT Pub. No.: WO2010/123821
PCT Pub. Date: Oct. 28, 2010

(65) Prior Publication Data
US 2012/0041472 A1 Feb. 16, 2012

Related U.S. Application Data (60) Provisional application No. 61/170,991, filed on Apr. 20, 2009.

(51) Int. Cl.
*A61M 29/00* (2006.01)
*A61B 17/12* (2006.01)
(Continued)

(52) U.S. Cl.
CPC ....... *A61B 17/12113* (2013.01); *A61B 17/1214* (2013.01); *A61B 19/54* (2013.01); *A61B 2017/00867* (2013.01); *A61B 2017/12054* (2013.01)
USPC ............ 606/200; 606/191; 606/157; 606/158

(58) Field of Classification Search
CPC ............................................. A61B 2017/12077
See application file for complete search history.

(56) References Cited

U.S. PATENT DOCUMENTS

| 5,026,607 | A | 6/1991 | Kiezulas | |
| 8,500,773 | B2 * | 8/2013 | Nardone et al. | 606/200 |
| 2006/0271153 | A1 * | 11/2006 | Garcia et al. | 623/1.11 |

(Continued)

FOREIGN PATENT DOCUMENTS

| FR | 2860705 | 4/2005 |
| WO | 99/32037 A1 | 7/1999 |

(Continued)

OTHER PUBLICATIONS

European Search Report and Opinion issued by the European Patent Office on Jul. 16, 2013 in co-pending EPO application.

*Primary Examiner* — Elizabeth Houston
*Assistant Examiner* — Todd J Scherbel
(74) *Attorney, Agent, or Firm* — Charles F. Reidelbach, Jr., Esq.

(57) ABSTRACT

A pusher-occlusive coil delivery assembly 10 that is advanced through a microcatheter 40 to the desired vascular site within a patient. The delivery assembly 10 includes a pushwire 12 which interlocks with the occlusive coil 11 which can be manipulated to detach the occlusive coil 11. When the assembly 10 is positioned at the site, the pushwire 12 is advanced to allow the interlock joint 14, 15 to move out of the delivery sleeve 13 to uncouple the pushwire 12 and the occlusive coil 11.

14 Claims, 5 Drawing Sheets

(51) Int. Cl.
*A61B 19/00* (2006.01)
*A61B 17/00* (2006.01)

(56) References Cited

U.S. PATENT DOCUMENTS

2008/0051831 A1 2/2008 Deal et al.
2008/0140089 A1* 6/2008 Kogiso et al. ............. 606/142
2008/0300667 A1 12/2008 Hebert et al.
2009/0036966 A1 2/2009 O'Connor et al.

FOREIGN PATENT DOCUMENTS

| WO | 2004/087006 | A2 | 10/2004 |
| WO | 2008/064205 | A2 | 5/2008 |

* cited by examiner

DELIVERY ASSEMBLY FOR OCCLUSION DEVICE USING MECHANICAL INTERLOCKING COUPLING MECHANISM

PRIORITY DOCUMENTS

This Application claims the benefit of U.S. provisional patent application Ser. No. 61/170,991, filed Apr. 20, 2009, which is incorporated herein by reference.

FIELD OF THE INVENTION

The present invention is related to a medical device and its use for delivery to a target site to create an intra-vascular embolism within the patient. More particularly, the invention relates to a delivery assembly, comprising a pushwire and an occlusive coil, wherein the pushwire and occlusive coil are releasably connected by a unique, mechanically interlocking configuration.

BACKGROUND

The use of an interventional apparatus such as a microcatheter assembly for placing occlusive devices, such as embolic coils, stents and dilation balloons, at target sites throughout the body have become standard procedures for endovascular disease treatment. Such approach is particularly useful in treating diseases that are located where traditional operational procedures pose a greater risk to the patient. Examples of these devices and their applications are shown in U.S. Pat. Nos. 5,261,916, 5,354,295 and 6,958,068, in which different methods of delivery and deployment of devices to sites, such as aneurysms are disclosed.

Embolic Coils such as those discussed in the above-mentioned documents are generally made of a radiopaque, biocompatible material typically metal such as platinum, tungsten, nitinol or alloys of these and other metals.

In treating peripheral or neural diseases such as aneurysm, typically, the procedures involve inserting a microcatheter over a guidewire into the vasculature and to a predetermined target site. Following the insertion of the microcatheter, an occlusive device, such as an embolic coil, attached at the distal end of a delivery assembly is then inserted through the lumen of the microcatheter towards the target site. Once the position of occlusive device at the target site is confirmed through radiological technique, the occlusive device is then detached from the delivery assembly to leave the occlusive device positioned at the target site. The detachment of the occlusive device is of utmost importance. Despite the technological advancement in the field of delivering occlusive devices to a target site, there are still problems associated with many of the current techniques. These problems include the ease of positioning and repositioning the occlusive coil before detachment, the accuracy in positioning the occlusive coil at the target site, and the duration of the deployment procedure.

In order to address the above-mentioned concerns, several different techniques are developed regarding the release mechanism of the occlusive device. Electrolytic detachment of an occlusive coil from a delivery wire is disclosed in U.S. Pat. Nos. 5,122,136 and 5,354,295. A metal occlusive coil is bonded to a dissimilar metal at the distal end of the delivery wire. Once the occlusive coil is deployed at the desired location, a small electrical current is passed through the guidewire and the occlusive coil will be detached via electrolysis. One advantage to this method is an improved accuracy of positioning the occlusive coil compared to detachment by mechanical force. However, several drawbacks make this technique less than optimal. One drawback is the need for accessories such as a power supply and electrical cables. Another drawback is that this is a time consuming technique because of the additional time required before the electrolysis reaction has sufficiently detached the occlusive coil. Furthermore, because of the electrical current, patients may experience discomfort during the electrolysis process.

An electrical resistance heating coil detachment procedure is disclosed in U.S. Pat. No. 6,478,773. The occlusive coil is mounted to the distal portion of the delivery assembly by a tubular collar that uses and electrical resistance coil that when heated will expand the collar and release the occlusive coil. This releasing procedure is similar to the electrolytic technique, discussed above, and similarly has the advantage of a highly accurate occlusive coil placement. Drawbacks again include the need for power supply accessories and the additional time required for the heat conduction to occur and the coil to be detached.

Hydraulic deployment is disclosed in U.S. Pat. Nos. 6,361,547 and 6,607,538. The occlusive coil is joined onto the microcatheter and a hydraulic injector or a syringe by attachment to the proximal end of the microcatheter. The occlusive coil can be released from the microcatheter when a fluid pressure as high as 300 pound per square inch (300 psi) is supplied through a lumen of the catheter, forcing the distal tip of the catheter to expand outward and in turn releasing the occlusive coil. The advantage of this method is the rapid detachment of the coil once the positioning of the coil is done. The drawback of this technique is the high hydraulic force introduced into the aneurysm which may led to potential rupture of the aneurysm.

Mechanical locking system between the coil and the delivery assembly is another type of deployment method which avoids the need for additional accessories during coil deployment. There are several types of interlocking mechanism for releasing an occlusive coil. Examples of such methods and apparatuses can be found in U.S. Pat. Nos. 5,261,916, 5,304,195, 5,350,397, 6,458,137 and 7,344,558.

One interlocking mechanism for embolic coil deployment is disclosed in U.S. Pat. No. 5,261,916. The pusher-embolic coil assembly has an interlocking ball and keyway coupling which can be manipulated in order to release the occlusive coil. Another similar mechanism is outlined in U.S. Pat. No. 5,304,195. The pusher-occlusive coil assembly of this patent has an interlocking ball and ball coupling which can be manipulated in order to release the occlusive coil. In another similar mechanism described in U.S. Pat. No. 5,350,397, the occlusive coil has an enlarged member such as a ball attached. The occlusive coil can be released by forcing the enlarge member through an aperture in a socket situated on the distal end of a pusher assembly. The device also include a plunger which is situated within the pusher housing which is use to force the occlusive coil out of the socket at the distal end of the assembly. The plunger can be activated axially or a screw driven device in which a knob can be rotated to push the ball out of the aperture of the socket and hence releasing the occlusive coil. The above-mentioned interlocking designs may all encounter similar drawback of the over-extension of the delivery assembly into the aneurysm causing damage to the wall of the aneurysm which may in turn led to further intracranial hemorrhage.

Another interlocking mechanism for occlusive coil deployment is disclosed in U.S. Pat. No. 6,458,137. The assembly comprises a delivery wire and the occlusive coil is attached onto the wire through thread and screw mechanism. The occlusive coil can be detached from the wire by rotating the wire so to unscrew the coil from the delivery wire. The drawback of this technique is the difficulty of rotating a long and thin delivery wire at the proximal end in order to release the occlusive coil at the distal end of the device.

Yet another interlocking mechanism for occlusive coil deployment is disclosed in U.S. Pat. No. 7,344,558. The delivery assembly includes a plunger which has a constrictor located at its distal end. The constrictor has a reduced size which grasps the occlusive coil. When the coil is ready to be deployed, the constrictor is rotated in an opposite direction to increase its size which in turn released the coil. Both U.S. Pat. Nos. 6,458,137 and 7,344,558 have similar rotating release mechanism which would encounter similar drawback of transferring the torque force from the proximal end to the distal end of the delivery assembly through the tortuous narrow neurovascular system.

The above discussion showed that even though various deployment methods are available, each and every method in the art has one or more of a variety of drawbacks. Therefore, a controlled, rapid and reliable deployment method for embolic coil without the need of external electrical power supply and the risk of further hemorrhage is needed in the art.

SUMMARY OF THE INVENTION

Briefly, and in general terms, the present invention presents a delivery assembly and methods for accurately and rapidly deploying an occlusion device at a target location within a patient. Preferably, the target location is within a patient's vasculature. The delivery assembly comprises an occlusive implant device that is an occlusive coil, a pushwire for pushing and deploying the occlusive coil through an elongated and flexible delivery sleeve, a first member of an interlocking mechanism, the first member being located at the distal end of the pushwire, and a second member of an interlocking mechanism, the second member being located at the proximal end of the occlusive coil. Optionally, the delivery assembly comprises a pushwire locking device located at the proximal end of the pushwire to prevent any relative movement between the pushwire and the delivery sleeve during delivery procedure. Optionally, two markers are attached to the delivery assembly in a configuration that allows for advancement of the pushwire through a delivery sleeve to the target site, but that contact each other to prevent over-extending of the pushwire/occlusive coil into the aneurysm. Preferably, the distal portion of the pushwire is coated with PTFE (Polytetrafluoroethylene) to provide a lubricous surface to aid the catheter in moving in the artery.

In one embodiment of the present invention, the occlusive coil is attached to the distal end of the pushwire of the delivery assembly through interlocking mechanism. The pushwire can be a tapered wire, tapered at its distal end to enhance pushability of said pushwire and to enhance trackability of the attached occlusive coil. In a preferred aspect of this embodiment, the interlocking mechanism comprises a first locking member and a second locking member. Preferably, said first locking member is a hook and said second locking member is a loop. Alternatively, said first locking member is a loop and said second locking member is a hook. The hook member is preferably a J-shaped hook, though alternative shapes such as Y-shapes, S-shapes and the like are useful.

In the preferred embodiment when the first locking member is a hook located at the distal end of the pushwire, said hook releasably interlocks with the loop of the second locking member located at the proximal end of the occlusive coil, when the interlocking mechanism is sufficiently located within the lumen of the distal end of the delivery sleeve. The occlusive coil can be deployed by advancing the pushwire, which is locked to the occlusive coil through engagement of the hook to the loop. The pushwire and the occlusive coil are advanced through the lumen of the delivery sleeve towards its distal end. As the interlocking joint exits the delivery sleeve lumen and thus is no longer confined within said lumen, the hook and loop disengage to release the occlusive coil. Disengagement of the hook from the loop is accomplished by a recoil action of the pushwire, said recoil action being facilitated through the shape of and material used in forming the distal end of said pushwire and the layer of lubricous PTFE covering the pushwire. At least the distal end of said pushwire is made of an elastic material, more preferably a super-elastic material, and said pushwire is formed with a bend at the distal end. The bend is sufficiently angled such that when confined within the lumen of the delivery sleeve, the bend is restricted. Once the distal end of the pushwire exits the end of the delivery sleeve, the bend causes a recoil movement in the pushwire. Thus, the advancement of a pushwire that is attached to an occlusive coil via an interlocking mechanism release the occlusive coil when the pushwire recoils to disengage the hook from the loop. The occlusive coil is then released from the delivery assembly at a target site.

Further, the invention advantageously incorporates a two marker system to enhance the precision of the deployment of the occlusive device to the target site. For this two marker system, there are attached markers to each of the pushwire and the delivery sleeve individually. Each of these markers may be made of a radiopaque material selected from platinum, gold, tungsten, rhenium, palladium, rhodium, and alloys thereof, or any combination thereof. The presence of two markers serves several purposes: First, a radiopaque marker is visible under radiographic conditions, thereby allowing the physician to identify the position of both the pushwire and the delivery sleeve to determine their relative positions within the microcatheter. Second, during deployment of the occlusive coil at the point when the interlocking joint is being pushed out from the delivery sleeve, the proximal marker, which is fixed onto the pushwire, will be pushed forward but will be blocked by the distal marker which is fixedly attached onto the inner surface of the delivery sleeve. This blocking prevents any further advancement of the pushwire into the aneurysm and prevents over-deployment of the pushwire into the target location. Using these radiopaque markers in such a configuration allows the occlusive coil to be precisely placed inside the aneurysm while also operating to prevent over-extending of the pushwire causing further injury to the aneurysm. Hence the two markers system acts as a safety catch to prevent over-extending of the pushwire.

Another aspect of this embodiment, one member of the interlocking mechanism is preferably formed at the distal end of the pushwire and comprises a hook-like shape, such as a J-shaped, and another member of the interlocking mechanism is preferably formed at the proximal end of the occlusive coil comprising an exposed loop. In this aspect, the delivery sleeve covers both the distal end of the pushwire and the proximal end of the occlusive device, thereby maintaining the interlocking mechanism in an attached configuration. The pushwire is preferably a material with at least elastic properties. Exemplary elastic materials include, but are not limited to nitinol (super-elastic), stainless steel (elastic), and alloys, or combination thereof. When the hook-and-loop interlocking joint is properly attached and is within the lumen of the delivery sleeve, it then enables the occlusive coil to be maneuver freely through the lumen of the microcatheter. Once the interlocked portion of the pushwire and occlusive coil is released from within the lumen of the delivery sleeve, the elasticity of the pushwire material flexes to separate the hook-like shape of the pushwire from the loop end of the occlusive coil. The pushwire is coated with PTFE to provide a lubricous surface to aid the catheter in moving in the artery. Preferably, the PTFE is in the form of a layer of lubricous coating or tubing, as is reasonably known in the art and further disclosed in U.S. Pat. No. 5,026,607, to enhance the pushability of the pushwire. Though it is preferred that the pushwire is configured to comprise the hook-like member and the occlusive coil is configured to comprise the loop member, this arrangement can be switched, and doing so is within the spirit of this currently disclosed invention.

Yet another aspect of this embodiment, the exposed loop at the proximal end of the occlusive coil can be formed during the manufacturing of the coil as an integral part of said coil. Alternatively, the proximal end loop portion can be manufactured or at a later stage of the process and attached to the already formed coil. In order to ensure satisfactory holding strength between the hook-and-loop joint, the open end of exposed loop is secured to the occlusive coil either by welding or using a suitable adhesive. The exposed loop can be a continuous portion of the occlusive coil or a separate part that is joined to the occlusive coil by welding or adhesive.

In another embodiment, the pushwire and first locking member at it distal end are entirely made of nitinol. Alternatively, the pushwire is a stainless steel tapered wire and the first locking member is a pre-shaped nitinol hook welded to the distal end of the pushwire. Preferably the first locking member is a hook shape. In order to take advantage of the super-elastic property of nitinol material, the hook is formed into a desired shape such as a J-, Y- or S-shape, the nitinol wire undergoes several shaping procedures. Briefly, in a first step, two thin nitinol wires are welded together, and then the welded wires undergo at least one heat treatment process to bend the welded wire and create the hook shape. When a hook member is engaged with a loop member to form an interlocking mechanism, the hook and loop remain engaged when confined within the lumen of a delivery sleeve. The super-elastic property of nitinol hook initiates release of the hook member from a loop member, when the surrounding pressure of the delivery sleeve lumen is removed. The degree that the hook-like member flexes during recoil is controlled by the heat treatment process that the nitinol wires underwent. Formation of a hook can be performed using a variety of other elastic or super-elastic materials. A similar shape formation procedure for nitinol is outlined in U.S. Pat. No. 6,569,193. Those skilled in art having the instantly disclosed invention in their possession will manufacture a locking mechanism using a variety of materials and techniques.

Another aspect of the invention is that the delivery sleeve is made of polymeric material comprising one or more of, Polyimide, polyether block amide, nylon, PTFE (Polytetrafluoroethylene), Polyetheretherketone (PEEK) and block copolymers thereof. Further, the delivery sleeve can be formed of two or more materials. For example, a proximal section of the delivery sleeve can be made of a first material and the distal section from a second material. A proximal section made of a polymide and a distal section made of nylon is a more specific example, though is provided only for illustration and not limitation. Additionally, the delivery sleeve can further comprise a reinforced wire to become braided tubing so to enhance the kink-resistance of the delivery sleeve. Alternatively, the surface of the delivery sleeve can further comprise of a layer of hydrophilic coating to enhance the trackability of the delivery assembly, which can be many different types of well-known hydrophilic polymer such as polyvinyl compounds, polyurethanes, polyacrylates or copolymers of vinyl compounds and acrylates or anhydrides, especially polyethyleneoxide, polyvinylpyrrolidone, and polyurethane. In a further alternative the lumen of said delivery sleeve can comprise a PTFE liner. Preferably, said PTFE liner provides a lubricated inner surface that facilitates navigation of a pushwire and occlusive device through said lumen of said delivery sleeve.

Yet another aspect of the invention there is provided a locking member at the proximal end of said delivery assembly. The proximal locking device can resemble to the torque device typically used for maneuvering guidewire or Rotating Hemostasis Valve (RHV). One example of an RHV is the guidewire holder from the QOSINA Inc. (Part #72990) Preferably, said locking member comprises two parts; the distal part is a housing that is fixed onto the delivery sleeve and the proximal part consists of a mechanical locking member that holds onto the pushwire, and the two parts are positioned such that the pushwire can be locked or released from the locking device. During a delivery procedure, the locking member is firmly locked to prevent any relative movement between the pushwire and the delivery sleeve. Once the occlusive coil is ready to be deployed, the locking member is released and the pushwire can be pushed forward for the occlusive coil to be deployed into the aneurysm.

The above is a brief description of some of the features of the present invention. Other aspects and advantages of the present invention will be illustrated from the following descriptions according to the various preferred embodiments of the present invention. The uniqueness of the various features and all the relevant information will be described in the accompanying drawings.

BRIEF DESCRIPTION OF THE DRAWINGS

Examples of the invention will be further explained with reference to the schematic drawings, in which.

DESCRIPTION OF THE PREFERRED EMBODIMENTS

Referring to the drawings introduced in the previous section, several embodiments of a delivery assembly are shown according to the principles of the present invention. However, the disclosed embodiments are merely exemplary of the invention which may be embodied in various forms. Details disclosed herein merely as a basis for claims and for teaching one skilled in the art to employ the present invention in any appropriate manner.

Figure 1:
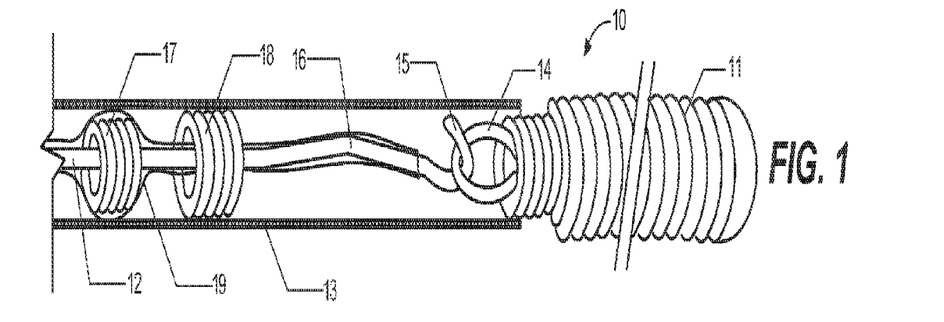
FIG. 1 is an enlarged, partially sectioned view of an embodiment of the delivery assembly of the invention illustrating the pushwire engaged to an occlusive coil through an interlocking mechanism; two markers and a delivery sleeve.

FIG. 1 illustrates a preferred embodiment of the pusher-occlusive coil assembly of present invention. The delivery assembly, generally designated as 10, comprises an occlusive coil 11 and a tapered pushwire 12 that is engaged with the occlusive coil 11 through interlocking mechanism 14 and 15. Said delivery assembly 10 can be confined inside the lumen of an elongated flexible delivery sleeve 13 which can be inserted into the vasculature of a patient for delivery of said occlusive coil 11 to a target site.

Figure 2:
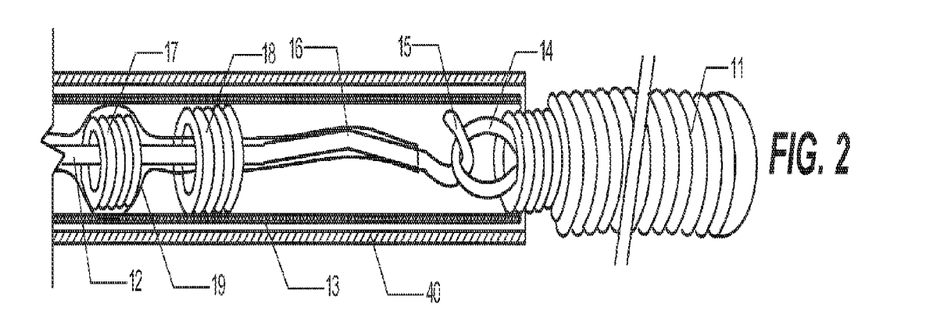
FIG. 2 is an enlarged, partially sectioned view of an embodiment of the delivery assembly as shown in FIG. 1 inside a microcatheter.

The interlocking mechanism comprises a first locking member 15 that is preferably a hook shape, and a second locking member 14 that is preferably a loop. Thus as illustrated in FIG. 1, the pushwire 12 comprises a hook 15 and the occlusive coil 11 is a loop 14, though the reverse configuration of hook and loop is an alternate embodiment. The proximal end of the occlusive coil 11 has an exposed loop 14 that is mechanically joined to a J-shaped hook 15 at the distal end of pushwire 12. A bend 16 in the distal portion of the pushwire 12 will facilitate the release of the occlusive coil 11. Pushwire 12 is preferably tapered. In the preferred embodiment, the pushwire 12 has a length in the range of 150 cm to 210 cm, more preferably 170 cm to 190 cm. The taper dimension is varied from the proximal end of pushwire 12 at about 0.008" to 0.015" in diameter to the distal end of pushwire 12 at about 0.002" to 0.005" in diameter. The pushwire 12 may be, but is not limited to carbon steel, 304V, 316L stainless steel, nitinol and alloys, or combination thereof; preferably the pushwire 12 is 304V stainless steel or super-elastic nitinol material. Using a metallic material such as 304V stainless steel, the hook 15 at the distal end of pushwire 12 and the bend 16 in the distal portion of the pushwire 12 can be formed mechanically to a predetermined shape using a fixture without the involvement of heat treatment process. The entire length or a portion of the pushwire 12 can further comprise a lubricious layer of PTFE coating so to improve the ease of advancing the pushwire 12. The pushwire 12 is coated with PTFE to provide a lubricous surface to aid the catheter in moving in the artery, as shown in FIGS. 1 and 2. Preferably, the PTFE is in the form of a layer of lubricous coating or tubing 19 to enhance the pushability of the pushwire 12.

In the embodiment of FIG. 1, a marker coil 17 is attached on the pushwire 12 positioned at a distance about 25 mm to 35 mm from the distal end of said pushwire 12. A layer of lubricous PTFE coating or tubing 19 covers the distal portion of the pushwire 12 including marker coil 17. A second marker coil 18 is located distal to the marker coil 17, and is fixedly attached onto the inner surface of the delivery sleeve 13, at a distance about 30 mm to 40 mm from the distal end of the delivery sleeve 13. Preferably, said markers 17 and 18 are radiopaque material. The relative positioning of the two markers 17 and 18 creates spacing between them when the occlusive coil 11 of the delivery assembly is positioned within the lumen of the delivery sleeve 13. During the deployment of the occlusive coil 11 to a target site, the pushwire 12 is moved distally, to protrude the occlusive coil 11 out of the delivery sleeve 13 and into the target site. The placement of markers 17 and 18 operate to control for over-extension of the pushwire 12 into the target site by bringing marker 17 into contact with stationary marker 18 and stopping the further deployment of the pushwire 12, thereby avoiding the risk of injuring the target site such as a feeble intracranial vessel wall of an aneurysm. Positioning of markers 17 and 18 on the pushwire 12 and in the delivery sleeve 13, therefore, are configured at distances that allow the occlusive coil 11, to be pushed into the target site but not over-deployed and thereby potentially damaging the target site. Once out of the lumen of the delivery sleeve 13 the occlusive coil 11 is mechanically detached from the pushwire 12. The J-hook 15 disengages from the loop member 14 to which it is interlocked by exiting the confinement of the delivery sleeve. Disengagement is further facilitated by the recoil action of the pushwire 12 upon release of bend 16 from the delivery sleeve 13. Each of markers 17 and 18 are made of a biocompatible radiopaque metal such as platinum, iridium, tungsten, and alloys thereof, which by using radiographic techniques allows for identifying the position of the delivery assembly within the delivery sleeve as it is being directed to a target location. The markers 17 and 18 can be joined to each of pushwire 12 and delivery sleeve 13 by welding, adhesive bonding or heat shrinkable tubing methods. Adhesive bonding can be a moisture cured cyanoacrylate adhesive such as Loctite 4011, 4161 or light cured adhesive such as Loctite 3321. Heat shrink tubing can be polyester or polyethylene heat shrink tubing.

The delivery sleeve 13 is a hollow elongated tube made of polymeric material that may be polyimide, polyether block amide, nylon, PTFE, PEEK and mixtures, or block copolymer thereof. The delivery sleeve 13 can comprise a variety of materials of different stiffnesses across the length of the sleeve, for example a stiff Pebax® 7233 at the proximal end, a medium stiffness Pebax® 5533 in the medium section and a soft Pebax® 2533 at the distal end of the delivery sleeve 13. The length of the delivery sleeve 13 will be in the range of 140 cm to 200 cm, preferably 160 cm to 180 cm. The inner diameter of the delivery sleeve 13 can be in a range of 0.008" to 0.018", preferably 0.010" to 0.016". Alternatively, the surface of the delivery sleeve 13 can further comprise of a layer of hydrophilic coating to enhance the trackability of the delivery assembly, which can be many different types of well-known hydrophilic polymer such as polyethyleneoxide, polyvinylpyrrolidone, and polyurethane. Alternatively, the delivery sleeve 13 can further comprise a braided polyimide or Pebax tubing of 304V stainless steel flat wire reinforcement with a pitch per inch of 60 to 100. Still further, the inner surface of the delivery sleeve can comprise a lubricious liner, which is preferably PTFE.

Figure 3:
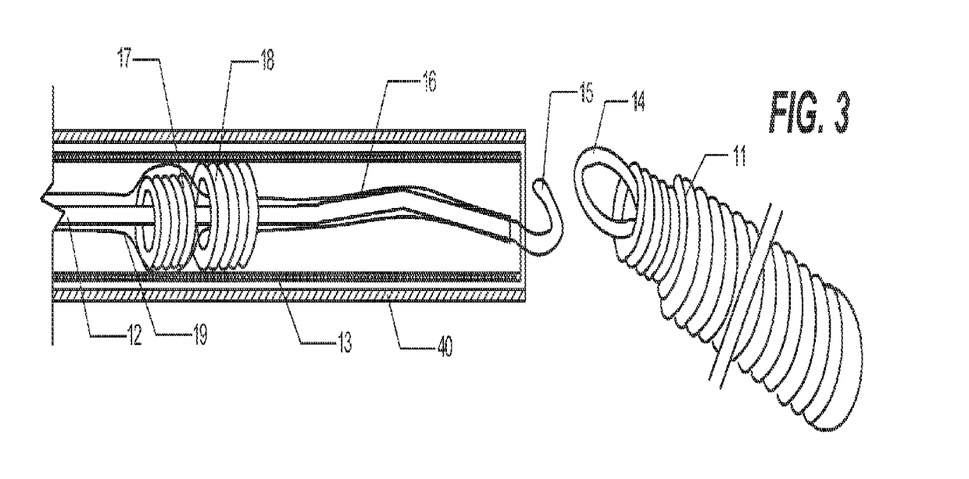
FIG. 3 is an enlarged, partially sectioned view of an embodiment of the delivery assembly as shown in FIG. 2, wherein the occlusive coil has been disengaged from the pushwire and thus released.

FIG. 2 illustrates the preferred embodiment of the delivery assembly inside a microcatheter 40 before a deployment procedure. The microcatheter 40 is inserted into the artery of the patient (not shown) to the target site to be occluded (e.g. aneurysm, vascular malformation or arteriovenous fistula). Conventional procedures involving guidewire and catheter insertion and navigation are used. The relative position of the radiopaque markers of the microcatheter 40 and the delivery assembly 10 are used for determining location of the delivery assembly using radiographic techniques. Once the distal end of the microcatheter 40 and the delivery assembly 10 of present invention are properly positioned at the target site, the occlusive coil 11 is ready to be deployed. The pushwire 12 is then pushed forward relative to the position of a delivery sleeve 13 (FIG. 3) for the occlusive coil 11 to be released. Once the interlock joint, comprising first locking member 15 and second locking member 14, is pushed outside of the delivery sleeve 13, the exposed loop 14 of the occlusive coil 11 disengages itself from the pushwire hook 15, which is further facilitated by elastic recoil at the bend 16 of the distal portion of pushwire 12, thereby releasing the occlusive coil 11 into the aneurysm. At the same time, the pushwire hook 15 is inhibited from over-extending into the target site by the marker 17 and marker 18 coming into contact with each other within the delivery sleeve (FIG. 3). Essentially, delivery sleeve 13 remains stationary relative to pushwire 12; the forward movement of pushwire 12 covered by the lubricous PTFE coating or tubing 19 causes the marker 17 to advance; advancement of marker 17 is limited by contacting marker 18, thus acting as a safety catch to prevent any further protrusion of the pushwire hook 15 out of delivery sleeve 13. Preferably, the dimension of the marker 17 (outer diameter about 0.006" to 0.010") is smaller than the dimension of marker 18 (outer diameter about 0.009" to 0.015") so to ensure smooth movement of the pushwire 12 during deployment. By altering the design of the relative distance between the two radiopaque markers 17 and 18, the extent of the protrusion of the pushwire hook 15 into the target site can be easily manipulated. The deployment system 10 is then withdrawn from the microcatheter 40 and the procedures are repeated for additional occlusive coils to be placed.

Figure 4:
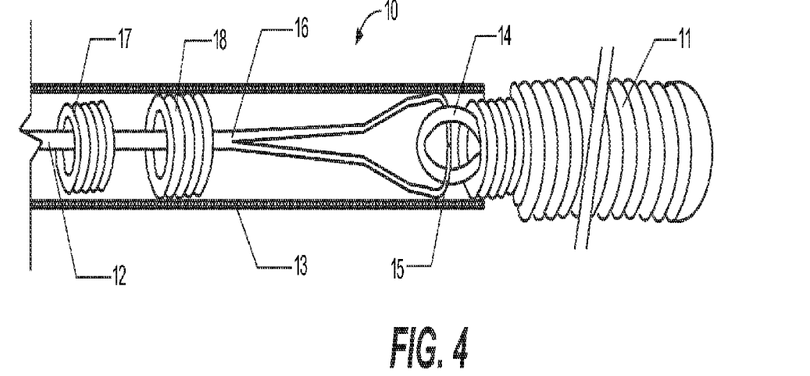
FIG. 4 is an enlarged, partially sectioned view of an alternative embodiment wherein a first locking member is a Y-shaped hook. In this FIG, the interlocking mechanism of the delivery assembly is confined within the lumen of the delivery sleeve, and thus engaged to the loop.
Figure 5:
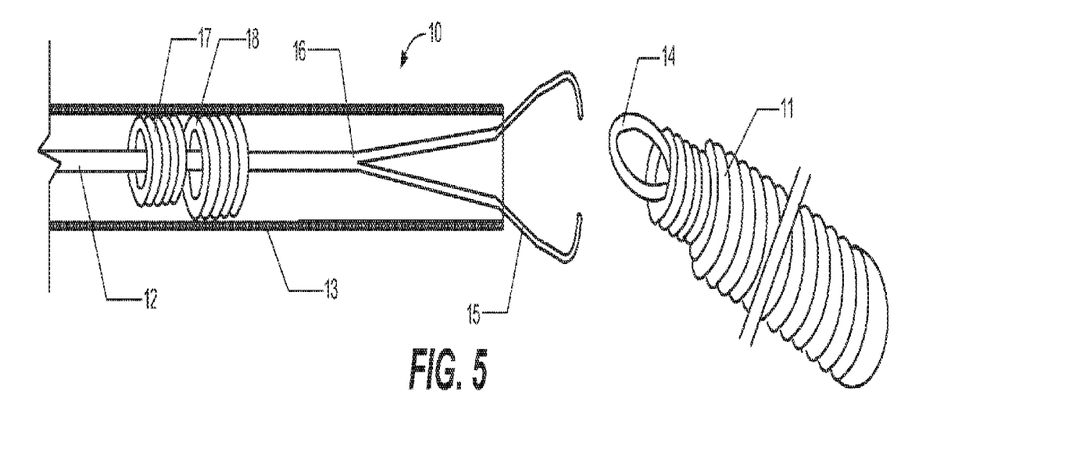
FIG. 5 is an enlarged, partially sectioned view of Y-shaped hook of FIG. 4. Here, the Y-shaped hook is deployed out of the delivery sleeve lumen, recoiled to an open configuration and thus released the loop of the occlusive coil.
Figure 6A:
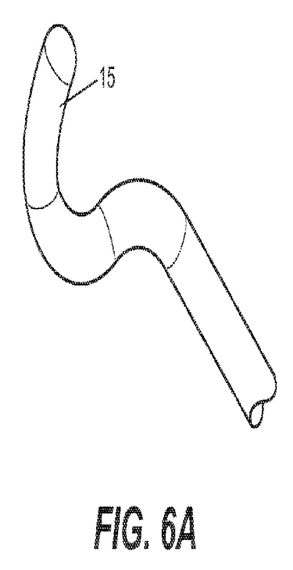
FIGS. 6A-C is a partial view of three embodiments of a locking member that is a hook; 6A is a J-shape; 6B is a Y-shape and 6C is an S-shape.
Figure 6B:
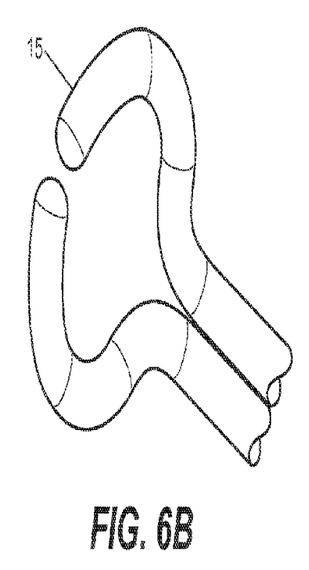
Figure 6C:
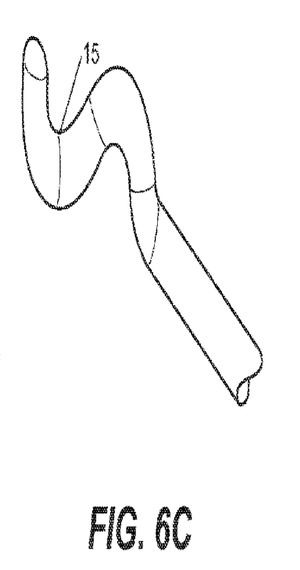

FIGS. 4-6 illustrate an alternative embodiment of the delivery assembly 10 in accordance with the present invention. In these embodiments, the pushwire 12 is preferably made of a material with super-elastic properties sufficient to undergo high degree of elastic deformation; one such example of such a material is nitinol. The entire pushwire 12 can be made of tapered nitinol wire or, the pushwire 12 can be made of a tapered stainless steel wire welded to a pre-shaped nitinol hook 15. In forming the J-shaped hook 15 using nitinol, nitinol wires of about 0.002" to 0.004" in diameter is fixed onto a mandrel or a J-shaped mold and then undergo one or more heat treatment processes in order to create the desired shape of the hook. The heat treatment process imparts the shape memory property to the wires, and preferably occurs at approximately 500° C. to 540° C. for 2 to 10 minutes. A three-stage heat treatment process may be performed in order to achieve the desired shape of the hook 15. (See e.g., U.S. Pat. No. 6,569,193).

In the embodiment shown in FIG. 4, a Y-shaped hook 15 is described. Here, the hook 15 member is a material with elastic properties, preferably super-elastic properties (e.g., nitinol). In this example, the pushwire 12 is stainless steel, and two nitinol wires are treated to form a Y-shaped hook 15, wherein the elastic property of the hook separate the arms of the Y-shaped hook 15 to disengage a loop 14. The Y-shaped hook 15 is welded to the bend 16 at the distal portion of the pushwire 12 by resistance or laser spot welding process. The occlusive coil 11 is secured to the deployment system 10 by interlocking an exposed loop 14 at the proximal end of the occlusive coil 11 with Y-shape hook 15. The Y-shaped hook 15 interlocks with the loop 14 when the hook 15 arms are placed near the loop 14 so that when the hook 15 arms are within the distal end of the delivery sleeve 13 they are constricted and thusly clamp the loop to interlock (FIG. 4). Once the interlock joint, comprising hook 15 and loop 14, is advance out of the delivery sleeve 13 (FIG. 5), the arms of the Y-shape hook 15 are no longer constricted by the lumen of the delivery sleeve 13 and so the hook 15 opens via material elasticity, and the loop bearing 14 occlusive coil 11 is released. The extent of the opening can be controlled by the heat treatment process that the nitinol wires underwent. Again, the pushwire 12 is designed to prevent over-extending into the site of deployment by using two markers 17 and 18 configured as discussed in the previous sections.

FIG. 6 illustrates various exemplary embodiments of the distal end of the delivery pushwire 12 forming the hook 15 of the present invention. Hook member 15 can be made of stainless steel, nitinol or other metal alloy that posses desired elastic or super-elasticity material property. Depending on the extent of the opening when the hook is pushed out into the deployment site, various design of the hook can be fabricated mechanically or using different molds and/or heat setting conditions. The distal end of the delivery pushwire 12 can comprise a hook member 15 that is designed in a J-shape, Y-shape or S-shape (FIG. 6). Preferably, the angle between the extended arms of the Y-shaped hoop is between 30 to 90 degrees. Other hook member 15 shapes and loop member 14 shapes forming an interlocking mechanism can be used, and an ordinarily skilled artisan in possession of this instant description will configure such alternative configurations. Such are within the spirit of the current invention. Shapes for hook member 15 are achieved using different mandrel or molds and/or different heat treatment process as described above.

Figure 7A:
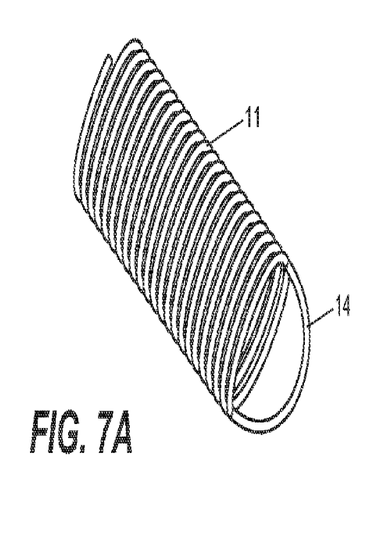
FIGS. 7A-B are embodiments of second locking members at the proximal end of the occlusive coil.
Figure 7B:
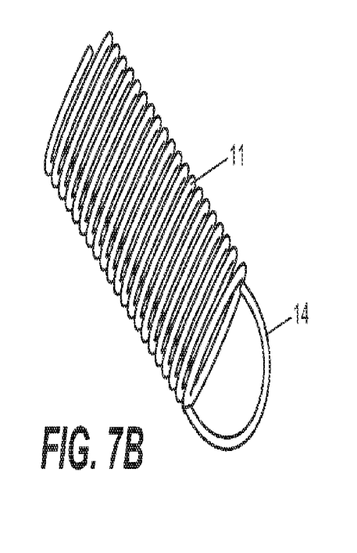

FIG. 7 illustrates various exemplary embodiments of the proximal end of the occlusive coil 11 forming the loop member 14 of the present invention. The exposed loop 14 and the occlusive coil 11 can both be made of a biocompatible material. Loop 14 and coil 11 can one or both be made of a biocompatible material comprising a radiopaque metal such as platinum, iridium, tungsten, and alloys thereof. The exposed loop 14 and the occlusive coil 11 can be made of a single continuous material, or the loop 14 can be a separate portion that is welded, glued or otherwise fixedly attached to the occlusive coil 11 portion.

Figure 8:
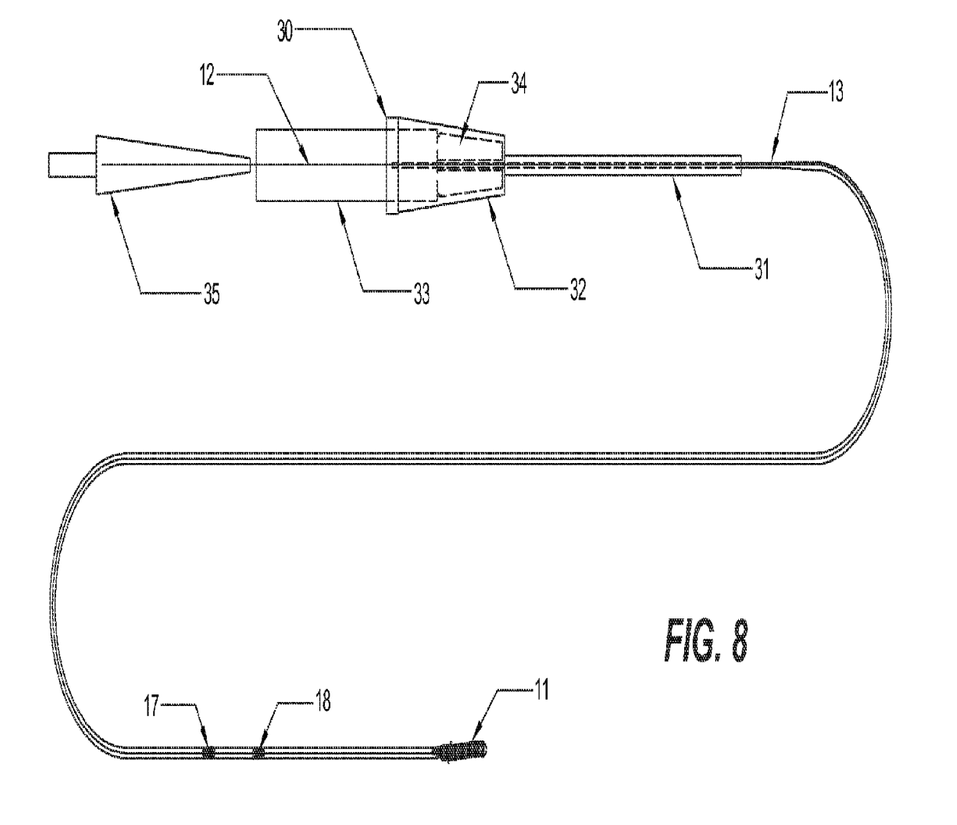
FIG. 8 is an enlarged, partially sectioned view illustrating the locking device at the proximal end of the delivery assembly.

FIG. 8 illustrates an embodiment of the locking device 30 at the proximal end of the pusher assembly. The locking device 30 is joined to the end of the delivery sleeve 13 by having a strain relief tubing 31 (e.g., a polymeric tubing) in-between and can be unlocked by turning when the occlusive coil 11 is to be detached. The locking device 30 which resemble the typical pushwire 12 torque device comprises a housing 32 fixedly attached to the strain relief tubing 31, a holding member 33 and a locking member 34. An end plug 35 is fixed at the proximal end of the pushwire 12 to facilitate the advancement of the pushwire 12. The inner diameter of the housing 32 is larger than the diameter of the pushwire 12 so to allow easy advancement of the pushwire 12 during deployment. The housing 32 is fixed onto a holding member 33 which can be screwed into an internally threaded bore in the housing. The threading action causes a locking member 34 inside the housing 32 to be radially compressed a channel running through the entire locking device 30. Therefore the pushwire 12 inserts through the channel can be locked by the locking device 30 and easily released by turning to the opposite direction. One such locking device is described in U.S. Pat. Nos. 6,458,137.

Figure 9A:
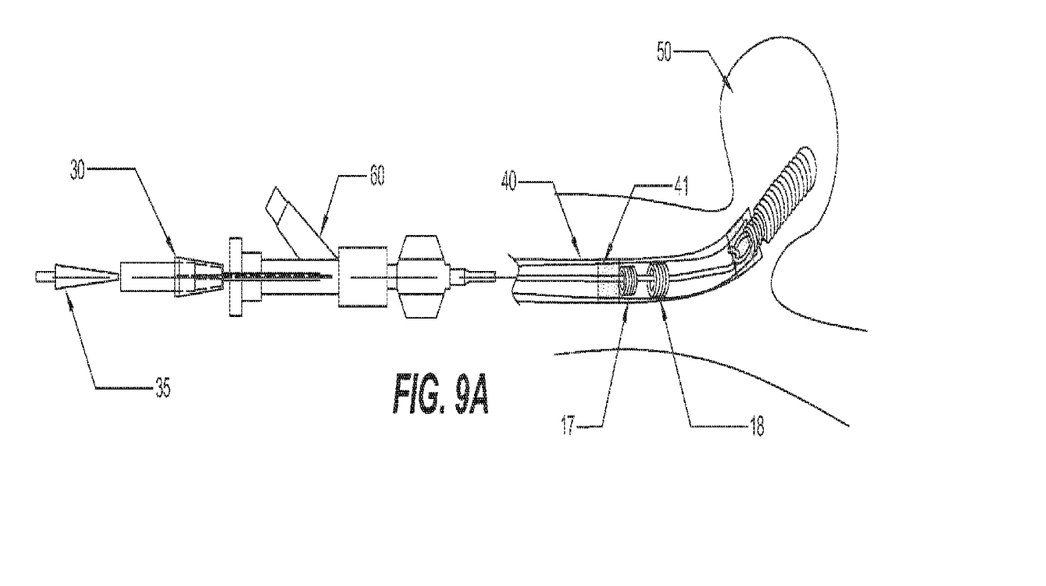
FIGS. 9A-B are illustrations of the deployment methods for placing an occlusive coil within the target site.
Figure 9B:
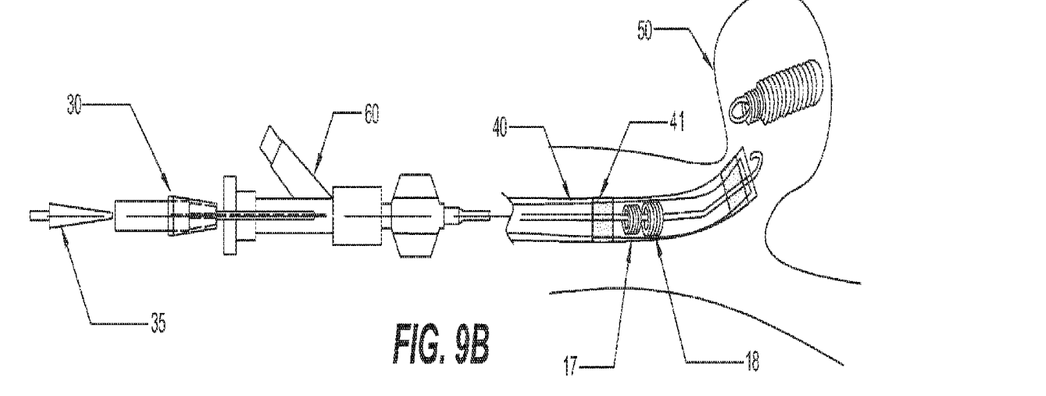

FIG. 9a-b illustrates the deployment methods for placing an occlusive coil 11 within the target site. Microcatheter 40 is inserted into the vasculature of a patient to the target site (50 in this illustration). The proximal end of the microcatheter 40 is attached with a Rotating Hemostasis Valve (RHV) 60. The main outlet of the RHV is for the insertion of the occlusive coil and the flushing solution such as saline is introduced through an outlet of the RHV.

After the microcatheter 40 has been properly placed at the target site 50, the delivery assembly 10 of the present invention is then inserted through the proximal end of the RHV 60 (FIG. 9a). Using a radiographic imaging system, such as Digital Subtraction Angiography (DSA), the delivery assembly 10 which includes the occlusive coil 11 is pushed into the microcatheter 40. The advancement will eventually cause the occlusive coil 11 to be fully inserted into the target site 50, whereby both radiopaque markers 17 and 18 on the delivery assembly 10 and within the delivery sleeve 13 coincide with a marker 41 on the microcatheter 40. Then, the housing 32 of the locking device 30 is unscrewed to release the pushwire 12. Delivery sleeve 13 is to remain stationary relative to the pushwire 12 so the occlusive coil 11 can be deployed by advancing pushwire 12 toward the target site 50. The deployment can be verified when pushwire 12 is prevented from being pushed any further because markers 17 and 18 have come into contact with each other. Additionally, it is preferred to confirm full deployment using DSA imaging to identify that both radiopaque markers 17 and 18 coincide with each other (FIG. 9*b*), thus helping to identify any problems preventing complete coil detachment, e.g., a kink in the delivery device. After the occlusive coil 11 has been deployed, the pushwire 12 and delivery sleeve 13 are withdrawn from the microcatheter through the proximal end of the RHV 60. Additional occlusive coils can be inserted into the deployment site following the above-mentioned procedures.

The above is a detailed description of several embodiments of the present invention. It is recognized that departures from the disclosed embodiments may be made within the scope of the invention. Modification to the device and the methods of using them will be apparent to those skilled in the art. The full scope of the invention is set out in the claims that follow. Accordingly, the claims and specification should not be construed to unduly narrow the full scope of protection to which the invention is entitled.

What is claimed is:

1. A delivery device for delivering an occlusive device to a target site, the delivery device comprising:
    a flexible delivery sleeve having an inner surface;
    a second radiopaque marker coil fixedly attached to the inner surface of the flexible delivery sleeve;
    an occlusive device having a second locking member;
    a pushwire including a proximal portion and a distal portion having a first locking member which is one of a single hook and a single loop, the first and second locking members are configured to be coupled before delivering the occlusive device, the pushwire configured to displace the first locking member to facilitate release of the occlusive device whereby the second locking member disengages from the first locking member in response to the distal portion of the pushwire exiting the confinement of the delivery sleeve; and
    a first radiopaque marker coil attached to the pushwire whereby contact engagement of the first marker with the second marker prevents over-extension of the pushwire out of the delivery sleeve.

2. The delivery device of claim 1 wherein the first locking member displaces distally but does not change shape during the release of the occlusive device.

3. The delivery device of claim 1 wherein the second locking member is a loop.

4. The delivery device of claim 1 wherein the single hook is a J-shaped hook.

5. The delivery device of claim 1 wherein the pushwire is composed of at least one material from the group consisting of carbon steel, stainless steel, nitinol, alloys thereof, and combinations thereof.

6. The delivery device of claim 1 wherein the proximal portion is composed of a first material and the distal portion is composed of a second material that is different than the first material.

7. The delivery device of claim 1 wherein each of the first marker and second marker include a material that is visible through a body portion under radiographic conditions.

8. The delivery device of claim 1 wherein the pushwire is coated with a friction-reducing material.

9. A method for delivering an occlusive device to a target site, said method comprising the steps of:
    a. traversing the delivery device of claim 1 towards a target site;
    b. distally displacing the occlusive device member of the delivery device out of a delivery sleeve lumen and into said target site; and
    c. disengaging the first locking device from the occlusive device.

10. A kit containing the delivery device of any of claims 1-7.

11. A delivery assembly for delivering an occlusive device to a target site, the delivery assembly comprising:
    a pushwire including a distal portion having a single hook;
    an occlusive device having a locking member configured to receive the single hook;
    a delivery sleeve having a distal end and defining a lumen;
    a first radiopaque marker coil attached to the pushwire;
    a second radiopaque marker coil attached to the delivery sleeve whereby contact engagement between the first marker coil and the second marker coil limit distal movement of the pushwire out of the delivery sleeve during a deployment of the occlusive device; and
    wherein the single hook is confined within the lumen and coupled to the locking member before the deployment of the occlusive device, the hook disengages from the locking member to which it is interlocked in response to the distal portion of the pushwire exiting a confinement of the delivery sleeve.

12. The delivery assembly of claim 11 wherein the hook substantially maintains its shape when the distal end of the pushwire exits the confinement of the delivery sleeve.

13. The delivery assembly of claim 11 wherein the first marker coil includes a material that is visible to an imaging system through a body during deployment of the occlusive device.

14. A method for delivering an occlusive device to a target site, said method comprising the steps of:
    a. traversing the delivery assembly of claim 11 towards a target site;
    b. distally displacing the occlusive device member of the delivery assembly out of the delivery sleeve lumen and into said target site; and
    c. disengaging the hook from the occlusive device.

* * * * *